United States Patent [19]

Shillington

[11] Patent Number: 5,178,322
[45] Date of Patent: * Jan. 12, 1993

[54] MULTIPLE CONFIGURATION DISPOSABLE SHARPS CONTAINER SYSTEM

[75] Inventor: Richard A. Shillington, Leucadia, Calif.

[73] Assignee: Med-Safe Systems, Inc., Carlsbad, Calif.

[*] Notice: The portion of the term of this patent subsequent to Oct. 13, 2009 has been disclaimed.

[21] Appl. No.: 701,202

[22] Filed: May 16, 1991

Related U.S. Application Data

[63] Continuation-in-part of Ser. No. 446,121, Dec. 5, 1989, abandoned.

[51] Int. Cl.⁵ .............................................. B65D 43/26
[52] U.S. Cl. ..................... 232/44; 232/43.3; 206/366; 220/908; 220/264; 220/335; 220/254
[58] Field of Search ................. 206/365, 366, 370; 220/908, 910, 262, 263, 264, 335, 254, 252; 232/43.1, 43.2, 43.3, 43.5, 44, 47, 62

[56] References Cited

U.S. PATENT DOCUMENTS

| | | | |
|---|---|---|---|
| 1,169,606 | 1/1916 | Blank et al. | 220/263 |
| 1,210,184 | 12/1916 | McIntyre | 220/254 |
| 1,333,051 | 3/1920 | Young | 220/908 |
| 1,638,360 | 8/1927 | Olson | 220/254 |
| 2,478,621 | 8/1949 | Attula | 220/262 |
| 4,674,677 | 6/1987 | Trautwein | 232/43.1 |
| 4,736,860 | 4/1988 | Bemis | 220/908 |
| 4,804,090 | 2/1989 | Schuh et al. | 206/366 |
| 4,809,850 | 3/1989 | Laible et al. | 220/908 |
| 4,828,107 | 5/1989 | Spencer | 206/366 |
| 4,953,732 | 9/1990 | Cocks | 220/262 |

FOREIGN PATENT DOCUMENTS

| | | | |
|---|---|---|---|
| 231291 | 8/1910 | Fed. Rep. of Germany | 220/335 |
| 477536 | 10/1915 | France | 220/335 |
| 473199 | 10/1937 | United Kingdom | 220/254 |

Primary Examiner—Stephen Marcus
Assistant Examiner—S. Castellano
Attorney, Agent, or Firm—Baker, Maxham, Jester & Meador

[57] ABSTRACT

A secure disposable container assembly for medical sharps and waste comprises the combination of a substantially rigid box-like lower housing defined by upstanding front, back, and side walls terminating with a top having an upwardly extending rectangular opening for providing access to the housing, and a top cover secured by locking tabs for permanent securement thereto, an elongated horizontally extending access opening in the top for receiving a disposable syringe or the like, and a pivotable closure for said opening pivotably mounted about said axis within said top and having a receptacle area normally exposed to said access opening in a first position for receiving a disposed article and a curved surface for covering said access opening upon pivoting from said first position to a second position for dumping said article into said housing.

18 Claims, 3 Drawing Sheets

MULTIPLE CONFIGURATION DISPOSABLE SHARPS CONTAINER SYSTEM

REFERENCE TO RELATED APPLICATION

The present application is a continuation-in-part of application Ser. No. 07/446,121, filed Dec. 5, 1989, and entitled "A Secure Container for Disposable Sharps", now abandoned.

BACKGROUND OF THE INVENTION

The present invention relates to disposable containers for hospital sharps and infectious waste, and pertains particularly to a secure disposable container and alternate closure assemblies for stand alone and for insert containers.

Hospitals and medical clinics use great quantities of sharps, such as needles, syringes, surgical blades, and the like, that are disposed of rather than cleaned and reused. It is necessary that the sharps be disposed of in a manner that prevents them being reused without sterilization. In particular, it is necessary to keep them from falling into the hands of those, such as intravenous drug users and the like, who are likely to use them without proper sterilization.

Numerous containers have been developed in recent years, which are reasonably secure and disposable for receiving and disposing of hospital sharps, wastes and the like. Many of these containers are disposable inserts that mount into a security housing which is lockable and is securely mounted on a wall or other support structure. Many of these insert containers however have an inadequate security closure built into it, and are out dated so that they do not provide adequate security against pilfering of used syringes and the like therefrom. While improved containers have been developed which cannot readily be reopened and articles cannot be easily removed therefrom, such containers must be kept in a secure place or securely mounted to non-removable structure to prevent unauthorized removal.

Many hospitals and clinics that have the older secure housings with insert type disposable containers do not wish to invest in new housings. It is therefore necessary to develop improved insert type disposable containers for these housings with improved closures for the combination. It is also desirable that new stand alone units be available.

An example of a prior art disposable insert type container and mounting housing is disclosed in U.S. Pat. No. 4,715,498 of Hanifl dated Dec. 29, 1987. This patent discloses a sharps container having a closure door that provides limited access to the interior of the container for mounting in a protective housing. However, an improved closure is desirable for such containers.

Examples of stand alone type containers are disclosed in U.S. Pat. No. 4,736,860, granted Apr. 12, 1988 to Bemis, and entitled SHARPS DISPOSAL CONTAINER, and in U.S. Pat. No. 4,828,107, granted May 9, 1989 to Spencer and entitled DISPOSABLE CONTAINER FOR SYRINGES. It is desirable that simpler more effective disposable containers be available.

In the manufacture of multiple related or similar products, it is desirable that as many parts be interchangeable as possible in order to reduce manufacturing costs. It is also desirable that different variations of the product be available to meet different conditions and needs. It is, therefore, desirable that an improved securable disposable container combination be available to provide both insert and stand alone containers.

SUMMARY AND OBJECTS OF THE INVENTION

It is the primary object of the present invention to provide an improved securable disposable container assembly.

In accordance with a primary aspect of the present invention, a secure disposable container assembly comprises a base container for receiving a first closure assembly for forming a stand alone unit for securely and detachably mounting to a support member, and a second closure assembly for providing a disposable insert container, both having an opening in a top front for receiving a disposable article and preventing access to the interior of the container by the human hand.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
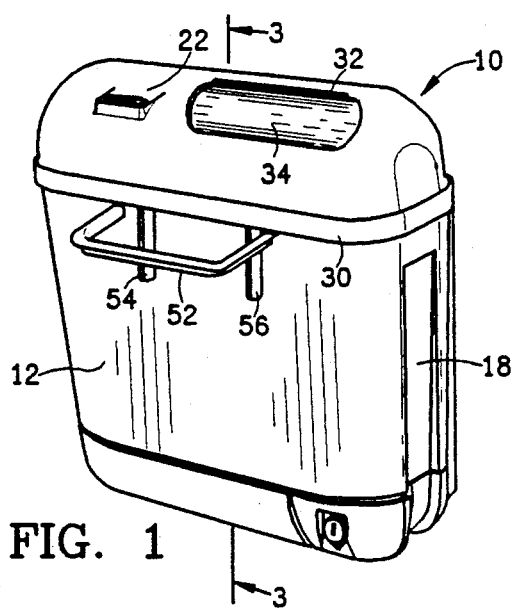
FIG. 1 is a perspective view of an exemplary embodiment of the invention.

Referring to FIG. 1 of the drawing, there is illustrated an exemplary embodiment of the invention, which comprises a generally rectangular open top container shell, designated generally by the numeral 10, and formed of the usual plastic material for such containers. The container in its preferred form is formed of a lower substantially rectangular box-like open top shell. The container has a front wall or panel 12 and a back wall or panel 14 (FIG. 2) defining front and back walls, and further including opposed side walls 16 and 18, all terminating at a top rectangular peripheral edge 20. The container is designed to receive alternate top cover or shell constructions to provide either a stand alone disposable container, as shown in FIG. 1, or a disposable insert for a protectable container as shown in FIG. 5. A generally semi-circular top shell 22 is mounted or attached to the top peripheral edge of the rectangular shell 10 to provide the stand alone configuration of FIGS. 1-5. A lower profile more open top shell provides the insert configuration of FIGS. 5-8.

The stand alone disposable container of FIGS. 1-4 will be described first. The top shell 22 and bottom are molded separately and utilize a plurality of snap lock tabs 24 (FIG. 5), for permanent attachment of the top to the top edge of the container. The snap lock tabs 24 extend slots 28 formed in the upper rim 20 of the container between the wall and downwardly extending skirt 30. The tab lock assembly includes tabs 26 on the top and tab sockets in the upper or top edge of the container to permanently lock the top 22 in the covering position, as shown in FIGS. 1 and 3.

A pair of attachment hinge tabs 26 are provided for connecting the top shell to the container in spaced relation, and allowing them to pivot relative to one another for providing a shipping mode of the container as will be described. The attachment hinge tabs 26 comprise a pair of downwardly directed prong hooks on the top shell for extending into and hooking under the edge of a pair of slots formed in the rim 20 of the container located above a pair of mounting slots.

Figure 2:
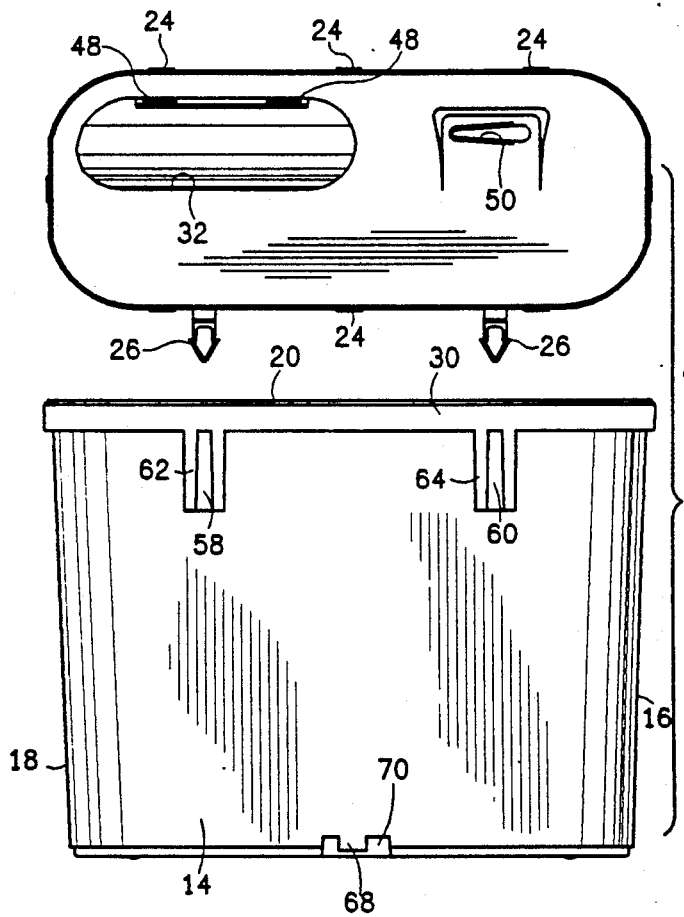
FIG. 2 is a rear elevation view of the embodiment of FIG. 1 with a top positioned for mounting.

The container top shell 22 and the bottom 12 are preferably separately blow molded of a suitable plastic, and later assembled. The container bottom 12 is preferably formed with a slight taper from top to bottom to enable stacking for ease of shipment. The top shell 22 has a generally semi-cylindrical configuration about a horizontal axis, about which a pivoting closure member 24 is mounted, as more specifically disclosed and described in the parent application. Referring to FIG. 2, the top shell 22 is provided with a top front opening 32 of a generally elongated configuration having circular or oval ends. This opening is formed in the upper front one side of the top extending approximately one-half the length of the top. This opening is designed to receive syringes and the like for disposal point first and includes a self-dumping closure 34 to secure the syringes against unauthorized retrieval.

Figure 3:
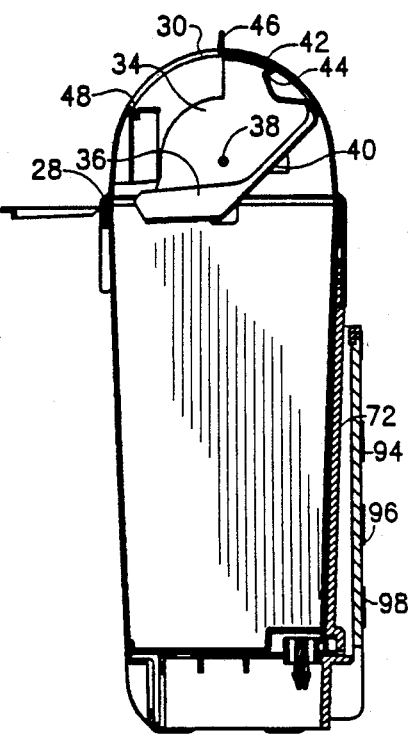
FIG. 3 is a side elevation view in section taken on line 3—3 of FIG. 1.

The opening is closed by a pivoting closure member or unit 34, as illustrated in FIG. 3, of a substantially unitary structure. The closure member 34 has a generally horizontal support face or ledge portion 36 disposed below the opening 30, and to one side of its pivot axis defined by a pair of pivot pins 38 at each end of the member 34. An upwardly extending face portion 40 forming a continuation of the face 36 extends upward at approximately a forty-five degree angle to a curved surface portion 42. These faces together form a combination closure and receiving support for disposable articles, such as a syringe or the like 38 as illustrated. The curved surface portion 42 extending backward from the upper or top edge of the face portion 38 thereby forms a closure for extending over the opening 32 when the closure member pivots about horizontal axis 38 for dumping an article.

The closure unit 34 is mounted for pivotal movement about a pair of pins, one at each end, which are rotatably mounted in snap in journals in the ends of the top shell 22. A counterweight is formed by wall portions 40 and 42 extending outward from the axis of the pivot pins and pivot axis of the unit opposite to the support surface 36, and biases the closure unit to its normally closed article receiving position. Once the container has been filled, the closure is forced or rotated to its closed position by grasping a hand recess 44 and forcing the closure such that curved closure portion 42 extends over the opening 32, and lock tabs 46 on an upper portion of the closure panel 42 extend into and lock into lock slots or sockets 48 formed in a small horizontal lip at the forward edge of the top shell opening 32. This essentially permanently locks the container in its closed position for disposal.

In normal operation, to dispose of a syringe as viewed in FIG. 1, the syringe is inserted into the top opening, needle first, with the needle extending toward the left to extend inside and underneath the top cover of the housing. The body of the syringe is placed on the horizontal closure surface 36, as seen in FIG. 3. The weight of the syringe overcomes the counterweight and tilts the closure member to automatically self-dump the syringe into the container. At the same time, the closure surface 42 moves forward and covers the opening 30 to prevent the insertion of a hand or the like for the removal of articles from the container.

If it is desirable to remove the needle to either reuse the syringe or prior to disposing of the syringe, a needle removal slot 50 is formed in the upper portion of the top for this purpose. This needle removal slot has a generally tear-drop configuration converging from a larger diameter at one end to a smaller diameter at the other. The slot has a pair of opposed tapered side walls, which act as wrench surfaces for engaging the side of a needle hub for applying torque for unthreading the needle.

The container is designed for ease of handling and to this end is provided with a retractable handle 52 that is preferably molded integrally with the lower edge of a peripheral rim or skirt 30. The handle 52 is pivotal outwardly, as shown for ease of grasping, and downward to a retracted position, engaging and latching to the lower ends of detent bars 54 and 56.

Referring to FIGS. 2 and 3, the back of the container is provided with means for attachment to a wall bracket to be described. The attachment means comprises a pair of hook slots 58 and 60 extending downwardly from the top back of the container. These slots are formed in an outer or outwardly spaced wall 62 and 64 of downwardly extending sockets formed on the back wall 14 of the container. The slots extend and hook over a pair of side walls on a mounting bracket 66, shown in FIGS. 3 and 4 as will be explained.

A latching tab 68 at the lower end of the back wall 14 extends downward and is biased by a cam or lever outwardly at about 90 degrees into latching engagement with a shoulder on and at the lower edge of the wall bracket for latching the container in place to the wall bracket. The tab 68 extends down at the outer edge of a cavity or recess 70 in the bottom back edge of the container.

Figure 4:
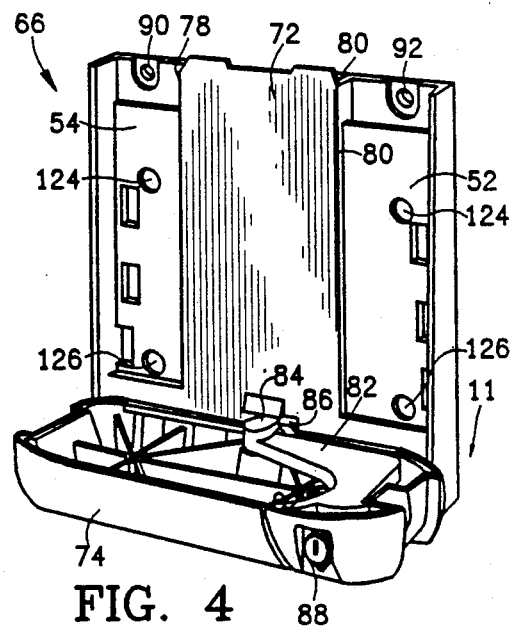
FIG. 4 is a perspective view of the mounting bracket for the embodiment of FIG. 1.
Figure 5:
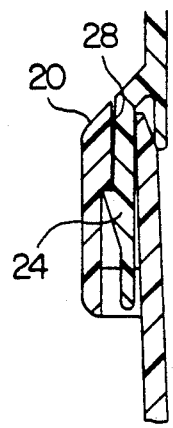
FIG. 5 is a view like FIG. 2 of an alternative top.

A wall mounting bracket is illustrated in FIG. 4, designated generally by the numeral 66, and is constructed to mount either to a vertical support surface or to a previously mounted bracket. The mounting bracket comprises a generally rectangular vertical panel, comprising a generally planar central panel 72 secured to and extending upwardly from a latching housing 74 to be described. The vertical panel comprises central panel 72 and forwardly stepped side panels 74 and 76 connected by forwardly extending side walls 78 and 80. The central panel 72 has an upper edge 72a which extends beneath the skirt 30 on the back of the container between slots 58 and 60. The forwardly extending walls 78 and 80 have upper edges (only 80a shown) which extend into and along slots 58 and 60 of the container. This arrangement of upper wall edges engages and supports the upper end of the container.

A lower housing 74 is permanently attached to or made integral with the vertical panel and houses the latching and locking mechanism. The panel 72 and the housing 74 are preferably made separately, such as by molding, and latched together by snap-fit latching means, not shown. The housing 74 is sized and shaped to form the appearance of an extension of the container and to cover the lower end thereof. The face of panel 72 facing the housing 74 is considered the front face of the panel for purposes herein. A latching lever or arm 82 (FIG. 4) is pivotally mounted in the housing 74 by a shaft and includes a latching cam or finger 84 on the inner end. The latching cam or finger engages tab 68 and biases it under and into engagement with latch surface 86 for latching the container in place.

The outer end of the arm 82 includes a lock assembly 88 that locks the lever 82 in the inner position. When the lever 82 is pivoted outward, cam or finger 84 is pulled away from shoulder 86, and the tab 68 is released so that the container may be lifted upward and removed from the mounting bracket. The lock assembly 88 is of conventional construction, having a key slot for receiving a key to rotate a shaft having a finger or arm, which in one position engages a shoulder in housing 74 for locking the arm in the inner position.

Figure 6:
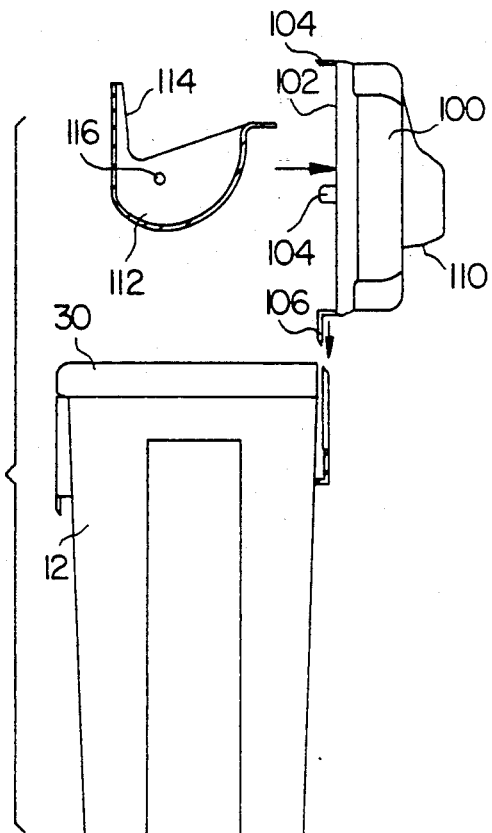
FIG. 6 is a side elevation exploded view of the embodiment of FIG. 5.

The mounting bracket 66 may be mounted to a vertical support surface, such as a wall by screws or lag bolts extending through mounting holes 90 and 92. It may also preferably be constructed to mount onto other mounting brackets. An exemplary embodiment of a typical wedge type bracket is illustrated in FIG. 6, of U.S. Pat. No. 4,736,860, and includes a panel having upper mounting holes and lower mounting holes for attachment by bolts or screws to a wall or the like. The panel includes a pair of non-parallel sides forming opposed downwardly diverging mounting rails for receiving a disposable container or the like.

The bracket 72 is provided with a series of opposing fingers along each side that engage the rails of the aforementioned bracket.

Figure 7:
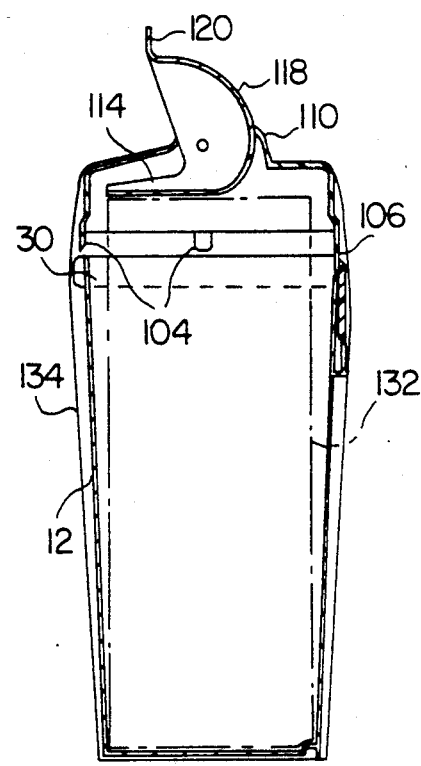
FIG. 7 is a side elevation view like FIG. 6 showing the container in an advanced stage of assembly.

Referring now to FIGS. 6-10, the disposable insert version of the disposable container for removably mounting in a protective housing will be described. This version, as previously mentioned, involves essentially the mounting of the different top cover or shell 100 on the same container 16 of the previous embodiment. As in the previous embodiment, the top cover or shell 100 contains a lower peripheral rim 102, having a plurality of locking tabs for permanent attachment of the top cover to the upper peripheral rim of the container. It also has a pair of hinge tabs 106 for spaced connection of the cover to the container. The top cover, as in the previous embodiment, also includes a pair of hinge tabs on one side, preferably the back side, which are elongated and permit the top cover to be attached to one side of the top rim of the container, and hingedly positioned over the container in spaced relation, substantially as shown in FIG. 7, for serving as a shipping container as will be subsequently described.

Figure 9:
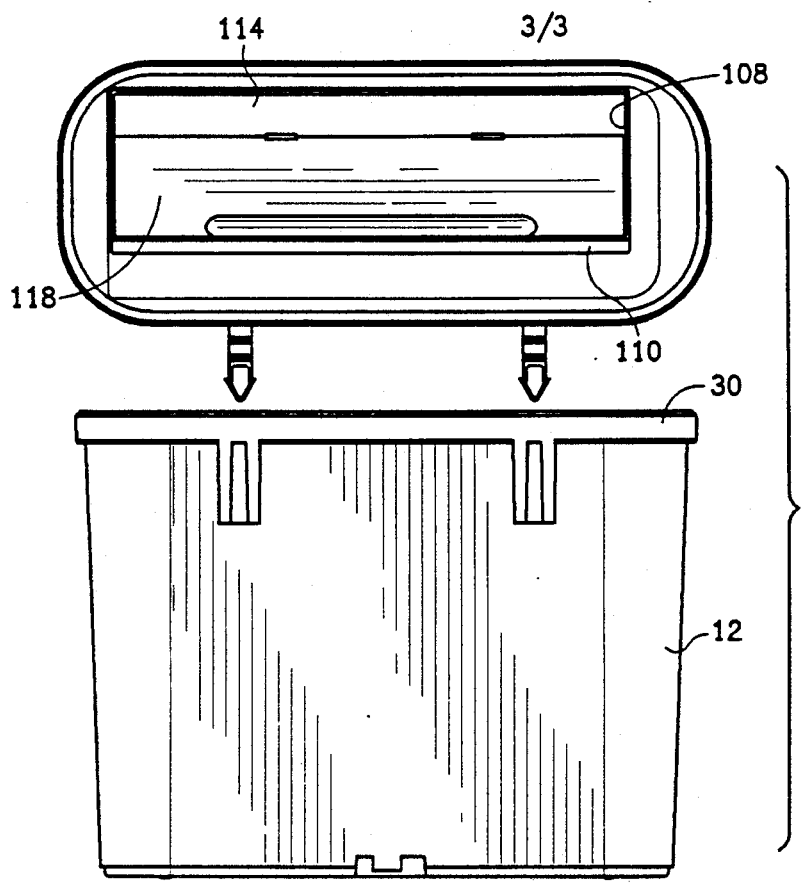
FIG. 9 is a front elevation view of the embodiment of FIG. 8.

Referring to FIG. 6, the top cover 100 comprises a generally rectangular top cover with rounded corners, as can be seen from the top view in FIG. 9, having an elongated slot opening extending substantially the long or longitudinal length of the top cover 100. The open slot is surrounded at the ends or sides and back by an upwardly extending shallow wall 110, as shown in FIGS. 6 and 7, for cooperatively receiving an elongated pivoting closure member 112 as illustrated.

The closure member 112 has a lower horizontally extending shelf or receptacle area 114 extending outward from one side of the axis as defined by a pair of pivoting pins 116 (only one shown) on the opposite ends thereof, and further including an upwardly extending curved portion 118 extending to the opposite side of the pivot axis, and upward therefrom to an upper transverse edge having a pair of locking tabs 120. The closure member is assembled in the top cover member as shown in FIG. 6, with the pins 116 extending into bearing mounts in the ends of the slot walls for pivotally mounting the closure member. The closure member has a normal slot closed position, as shown in FIG. 7, with the receptacle area 114 disposed horizontally for receiving a syringe or like article for disposal. The closure member is responsive to the positioning of a syringe or article on the receptacle area 114 to self dump the article, i.e., it is pivoted about its axis 116 downward to dump the article into the container, while the curved portion 118 of the closure extends or pivots over and closes the opening 108.

Figure 8:
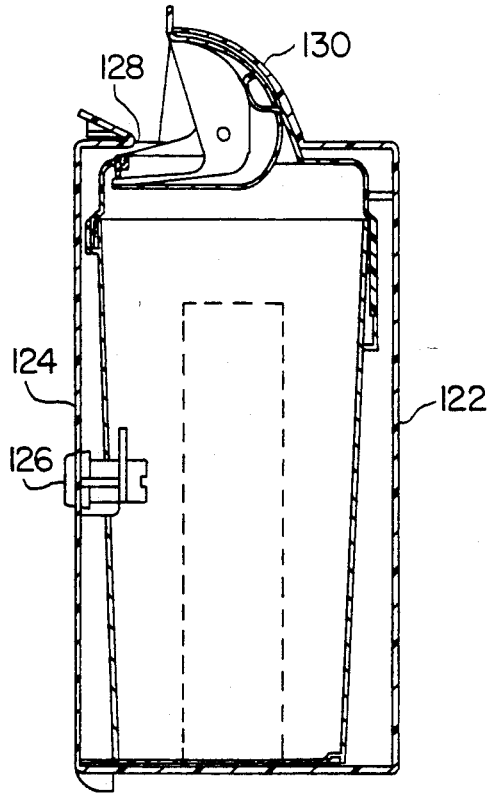
FIG. 8 is a side elevation view in section of the embodiment of FIG. 5 in a protective housing.
Figure 10:
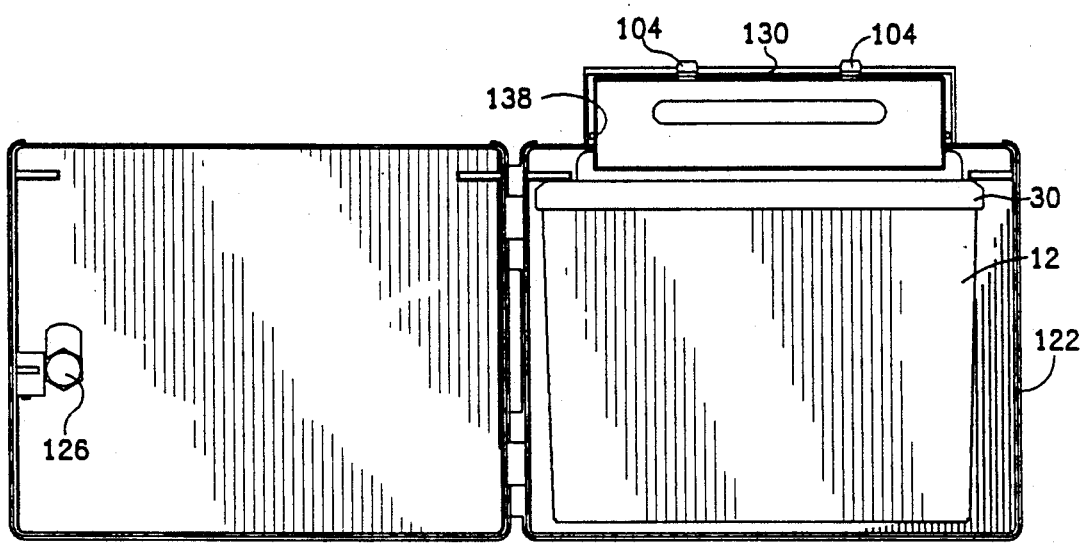
FIG. 10 is an enlarged section view of a top connection lock tab.

This container combination is designed as a disposable insert for certain existing housings, as illustrated in FIGS. 8 and 10, wherein a rectangular box-like housing 122 has a front openable door 124, with locking means 126 for opening the front of the housing for access thereto. The housing has an upper opening slot 128, with a curved cowling or protective shield 130 extending over the top of the slot 128. The top 100 is designed with its opening to fit this opening, with closure member 116 protectively extending under the shield 130. In the illustrated arrangement, the disposable container is protectively positioned and retained within the protective housing 122, with the two openings in registration.

Thus, the above described system provides a construction wherein one container top cover can be utilized to provide a stand alone disposable container, and a second closure cover top can be utilized to provide a disposable insert for a protective housing. As in the previous embodiment, when the container has become full of disposable articles, the closure is pivoted forward, such that the top curved portion extends over the opening, and the lock tabs at the forward edge thereof are extended into and locked into locking slots at the forward edge of the cover opening. The container may then be disposed of in the usual manner.

An alternate feature of the present invention is a construction of both embodiments which enable the containers to be shipped in volume in a nested fashion, with the top cover attached by the two elongated tabs at the back and the top hinged over to one side (not shown). In an alternate arrangement, the container can serve as a shipping container, with the top positioned over and spaced above the top peripheral edge of the container, to accommodate a container 132 as illustrated in FIG. 7, and secured by a banding strap 134 in that manner to provide a closed shipping container. The carton 132 is preferably high enough to support the top 100 in spaced relation above the container, so that attachment tabs 104 do not extend into the slots. When the container reaches its destination, the customer removes strapping bands, the contents of the container, and then positions and attaches the cover directly to the upper rim of the container. This may be utilized, for example, for shipping a supply of syringes to a hospital clinic or the like. Thus, each container may serve as a shipping container for a quantity of syringes which would normally fill the container in its disposed configuration. Thus, each shipped supply or package of syringes is provided with its own disposable container shipped therewith in a compact efficient arrangement.

While I have illustrated and described my invention by means of specific embodiments, it is to be understood that numerous changes and modifications may be made therein without departing from the spirit and scope of the invention as defined in the appended claims.

I claim:

1. A secure disposable container assembly for disposal of medical sharps, comprising:
    an open top container defined by a bottom, a front wall, a back wall, and opposed side walls integral with and extending upward from said bottom terminating in an upper peripheral rim defining an upwardly directed rectangular opening, said upper peripheral rim includes a plurality of slots formed therein;
    an elongated top cover having a longitudinal central axis having a front side and a back side and a lower peripheral edge with means for attachment to said upper peripheral rim for covering said upwardly directed rectangular opening, said lower edge includes a plurality of locking tabs for extending into said slots for attaching said top cover to said container, including a pair of elongated tabs for attaching one side of said top cover to said container in spaced relation thereto for defining a shipping mode of said container;
    an elongated opening in said top cover disposed predominately on said front side of said central axis for receiving medical sharps; and
    an elongated pivoting closure pivotally mounted about said longitudinal central axis within said top cover and comprising a receptacle area having a width about equal to the radius of said top cover normally disposed in a first position extending horizontally outward from proximate said central axis to a wall of said top cover solely on said front side of said central axis for normally closing said elongated opening and for receiving a disposable article and self-dumping in response thereto, and a curved portion joined to and extending upward from proximate said axis to a position above and on said back side of said central axis from said receptacle area for and responsive to pivoting of said closure in response to said article on said receptacle area for moving to a second position over and covering said elongated opening for preventing access to the interior of said container.

2. A secure disposable container assembly for disposal of medical sharps, comprising:
    an open top container defined by a bottom, a front wall, a back wall, and opposed side walls integral with and extending upward from said bottom terminating in an upper peripheral rim defining an upwardly directed rectangular opening;
    an elongated top cover having a longitudinal central axis having a front side and a back side and a lower peripheral edge with means for attachment to said upper peripheral rim for covering said upwardly directed rectangular opening;
    an elongated opening in said top cover disposed predominately to said front side of said central axis for receiving said medical sharps; and
    an elongated pivoting closure pivotally mounted about said longitudinal central axis within said top cover and comprising a receptacle area having a width about equal to the radius of said top cover normally disposed in a first position extending from proximate said axis horizontally outward solely to said front side of said central axis for normally closing said elongated opening and for receiving a disposable article and self-dumping in response thereto, and a curved portion jointed to and extending upward from proximate said central axis to a position above and on the back side of said central axis for and responsive to pivoting of said closure in response to said disposable article on said receptacle area for moving to a second position over and covering said elongated opening for preventing access to the interior of said container wherein said closure comprises an elongated member extending the length of said top, and said curved portion is defined by a semi-cylindrical portion extending along the axis thereof.

3. A secure disposable container assembly according to claim 2 wherein said top cover is semi-cylindrical in configuration curving about said {generally horizontal} central axis, and said {access} elongated opening in said top cover extends from one end to proximate the center thereof.

4. A secure disposable container assembly for disposal of medical sharps, comprising:
    an open top container defined by a bottom, a front wall, a back wall, and opposed side walls integral with and extending upward from said bottom terminating in an upper peripheral rim defining an upwardly directed rectangular opening;
    an elongated semi-cylindrical top cover having a longitudinal central axis having a front side and a back side and a lower peripheral edge with means for attachment to said upper peripheral rim for covering said upwardly directed rectangular opening;
    an elongated opening in said to cover extending from one end to proximate the center thereof and disposed predominately to said front side of said central axis for receiving said medical sharps; and
    an elongated pivoting closure pivotally mounted about said longitudinal central axis within said top cover and comprising a receptacle area having a width about equal to the radius of said top cover normally disposed in a first position extending from proximate said axis horizontally outward solely to said front side of said central axis for normally closing said elongated opening and for receiving a disposable article and self-dumping in response thereto, and a curved portion joined to and extending upward from proximate said central axis to a position above and on the back side of said central axis for and responsive to pivoting of said closure in response to said disposable article on said receptacle area for moving to a second position over and covering said elongated opening for preventing access to the interior of said container wherein said closure comprises an elongated member extending the length of said top, and said curved portion is defined by a semi-cylindrical portion extending along the axis thereof;
    a mounting bracket for mounting said container to a supporting structure comprising a generally rectangular back panel having first attaching means for attachment to a vertical support structure; and
    latching means at a lower edge of said back panel comprising a horizontally extending ledge, and a lower actuated cam for biasing a tab on said container into latching engagement with said ledge.

5. A secure disposable container assembly according to claim 4 wherein:

said back panel includes second mounting means for mounting said panel on said second mounting means.

6. A secure disposable container assembly according to claim 2 wherein:
said elongated opening is an elongated horizontally extending slot extending substantially the length of said top cover; and
said curved portion of said pivoting closure extends from said elongated opening above said top cover.

7. A secure disposable container assembly according to claim 6 wherein:
said pivoting closure includes locking means comprising tabs on said pivoting closure for engaging slots in said top cover at a lower edge of said elongated opening for permanently locking said pivoting closure in said second position.

8. A secure disposable container assembly for disposal of medical sharps, comprising:
an open top container defined by a bottom, a front wall, a back wall, and opposed side walls integral with and extending upward from said bottom terminating in an upper peripheral rim defining an upwardly directed rectangular opening;
an elongated top cover having a longitudinal central axis having a front side and a back side and a lower peripheral edge with means for attachment to said upper peripheral rim for covering said upwardly directed rectangular opening;
an elongated opening in said top cover defined by an elongated horizontally extending slot extending substantially the full length of said top cover and disposed predominately to said front side of said central axis for receiving said medical sharps;
an elongated pivoting closure pivotally mounted about said longitudinal central axis within said top cover and comprising a receptacle area having a width about equal to the radius of said top cover normally disposed in a first position extending from proximate said axis horizontally outward solely to said front side of said central axis for normally closing said elongated opening and for receiving a disposable article and self-dumping in response thereto, and a curved portion joined to and extending upward from proximate said central axis through said elongated opening to a position above said top cover and on the back side of said central axis for and responsive to pivoting of said closure in response to said disposable article on said receptacle area for moving to a second position over and covering said elongated opening for preventing access to the interior of said container, wherein said closure comprises an elongated member extending the length of said top, and said curved portion is defined by a semi-cylindrical portion extending along the axis thereof; and
an outer housing having a chamber and an access door for mounting said container in said housing, said housing having a top housing cover with an access slot for alignment with said elongated horizontally extending slot in said top cover of said container, and a curved cowling extending over said access slot and said curved portion of said pivoting closure.

9. A multiple mode secure disposable container assembly for disposal of medical sharps, comprising:
a substantially rigid open top container defined by a bottom, a front wall, a back wall, and opposed side walls integral with and extending upward from said bottom terminating in an upper peripheral rim defining an upwardly directed rectangular opening;
a plurality of attachment slots formed in said upper peripheral rim for attachment of an elongated top cover;
said elongated top cover having a longitudinal central axis having a front side and a back side and a lower peripheral edge with a plurality of first locking tabs for extending into a first set of said attachment slots for attachment of said cover to said container in spaced relation for defining a shipping mode of said container, a second plurality of locking tabs for extending into a second plurality of said slots for attaching said top cover to said upper peripheral rim for covering said upwardly directed rectangular opening;
an elongated horizontally extending access opening in said top cover disposed predominately to said front side of said central axis for receiving said medical sharps; and
an elongated horizontally extending self dumping closure member extending the length of said top cover pivotally mounted about said central axis within said top cover and comprising a receptacle area having a width about equal to the radius of said top cover normally disposed in a first position extending horizontally outward from proximate said central axis solely to said front side of said central axis to a wall of said top cover and directly below said access opening for normally closing said access opening and for receiving a disposable article, and a curved portion joining said receptacle area proximate said central axis and extending upward from and on the back side of said central axis and responsive to pivoting of said closure member to a second position in response to said disposable article on said receptacle area for moving over and covering said access opening for preventing access to the interior of said container, said closure member includes locking means for permanently locking said closure member in said second position.

10. A secure disposable container assembly according to claim 9 wherein said top cover is semi-cylindrical in configuration curving about said longitudinal central axis, and said access opening in said top cover extends from one end to proximate the center thereof for defining a self-contained mode of said container.

11. A secure disposable container assembly for disposal of medical sharps, comprising:
a substantially rigid open top container defined by a bottom, a front wall, a back wall, and opposed side walls integral with and extending upward from said bottom terminating in an upper peripheral rim defining an upwardly directed rectangular opening;
a plurality of attachment slots formed in said upper peripheral rim for attachment of an elongated semi-cylindrical top cover;
said elongated top cover having a longitudinal central axis having a front side and a back side and a lower peripheral edge with a plurality of first locking tabs for extending into a first set of said attachment slots for attachment of said cover to said container in spaced relation for defining a shipping mode of said container, a second plurality of locking tabs for extending into a second plurality of said slots for attaching said top cover to said upper peripheral rim for covering said upwardly directed rectangular opening;

an elongated horizontally extending access opening in said top cover extending from one end to proximate the center thereof and disposed predominately to said front side of said central axis for receiving said medical sharps and defining a self-contained mode of said container;

an elongated horizontally extending self dumping closure member extending the length of said top cover pivotally mounted about said central axis within said top cover and comprising a receptacle area having a width about equal to the radius of said top cover normally disposed in a first position extending horizontally outward from proximate said central axis solely to said front side of said central axis to a wall of said top cover and directly below said access opening for normally closing said access opening and for receiving a disposable article, and a curved portion joining said receptacle area proximate said central axis and extending {outward and} upward from and on the back side of said central axis and responsive to pivoting of said closure member to a second position in response to said disposable article on said receptacle area for moving over and covering said access opening for preventing access to the interior of said container, said closure member includes locking means for permanently locking said closure member in said second position;

a mounting bracket for mounting said container to a supporting structure comprising a generally rectangular back panel having first attaching means for attachment to a vertical support structure; and latching means at a lower edge of said back panel comprising a horizontally extending ledge, and a lower actuated cam for biasing a tab on said container into latching engagement with said ledge.

12. A secure disposable container assembly according to claim 9 wherein:

said top cover has a substantially flat top surface and said access opening is an elongated horizontally extending slot extending substantially the length of said top cover; and said curved portion of said self-dumping closure member extends from said access opening above said top cover for defining a disposable insert mode of said container.

13. A secure disposable container assembly for disposal of medical sharps, comprising:

a substantially rigid open top container defined by a bottom, a front wall, a back wall, and opposed side walls integral with and extending upward from said bottom terminating in an upper peripheral rim defining an upwardly directed rectangular opening;

a plurality of attachment slots formed in said upper peripheral rim for attachment of an elongated top cover having a substantially flat top surface;

said elongated top cover having a longitudinal central axis having a front side and a back side and a lower peripheral edge with a plurality of first locking tabs for extending into a first set of said attachment slots for attachment of said cover to said container in spaced relation for defining a shipping mode of said container, a second plurality of locking tabs for extending into a second plurality of said slots for attaching said top cover to said upper peripheral rim for covering said upwardly directed rectangular opening;

an elongated horizontally extending access opening defined by a slot in said top cover extending substantially the length thereof and disposed predominately to said front side of said central axis for receiving said medical sharps; and an elongated horizontally extending self dumping closure member extending the length of said top cover pivotally mounted about said central axis within said top cover and comprising a receptacle area having a width about equal to the radius of said top cover normally disposed in a first position extending horizontally outward from proximate said central axis solely to said front side of said central axis to a wall of said top cover and directly below said access opening for normally closing said access opening and for receiving a disposable article, and a curved portion joining said receptacle area proximate said central axis and extending upward from from said access opening above said top cover and on the back side of said central axis for defining a disposable insert mode of said container and responsive to pivoting of said closure member to a second position in response to said disposable article on said receptacle area for moving over and covering said access opening for preventing access to the interior of said container, said closure member includes locking means for permanently locking said closure member in said second position;

an outer housing having a chamber and an access door for mounting said container in said housing, said housing having a top housing cover with an access slot for alignment with said elongated horizontally extending access opening in the top cover of said container, and a curved cowling extending over said access slot and said curved portion of said pivoting closure.

14. A secure disposable container assembly according to claim 9 wherein:

in said shipping mode, a shipping carton is disposed in said container, and a banding strap extends around said container and said top cover for holding said top cover in said spaced relation against said carton.

15. A multiple mode secure disposable container system for disposal of medical sharps, comprising:

a substantially rigid open top container defined by a bottom, a front wall, a back wall, and opposed side walls integral with and extending upward from said bottom terminating in an upper peripheral rim defining an upwardly directed rectangular opening;

a plurality of attachment slots formed in said upper peripheral rim for receiving attachment tabs for attachment of an elongated top cover thereto;

said elongated top cover having a longitudinal central axis having a front side and a back side and a lower peripheral edge with a plurality of first attachment tabs for extending into a first set of said attachment slots for attachment of said cover to said container in spaced relation for defining a shipping mode of said container for accommodating a shipping carton therein, a second plurality of attachment tabs for extending into a second plurality of said slots for attaching said top cover to said upper peripheral rim for secure covering of said upwardly directed rectangular opening;

an elongated horizontally extending slot defining an access opening in said top cover disposed predominately on said front side of said central axis for providing access to the interior of said container for receipt of said medical sharps therein; and an elongated horizontally extending self-dumping closure member extending the length of said top cover pivotally mounted about said central axis within said top cover and comprising a receptacle area having a width about equal to the radius of said top cover normally disposed in a first position horizontally outward solely on said front side of said central axis and directly below said access opening for normally closing said opening and for receiving a disposable article, and a curved portion extending upward from proximate and on said back side of said central axis and responsive to pivoting of said closure member to a second position in response to said disposable article on said receptacle area for moving over and covering said access opening for preventing access to the interior of said container, said closure member includes locking means for permanently locking said closure member in said second position.

16. A secure disposable container assembly according to claim 15 wherein:

said top cover is semi-cylindrical in configuration curving about said central axis, and said access opening in said top cover extends from one end to proximate the center thereof for defining a self-contained mode of said container;

a mounting bracket for mounting said container to a supporting structure comprising a generally rectangular back panel having first attaching means for attachment to a vertical support structure; and latching means at a lower edge of said back panel comprising a horizontally extending ledge, and a lever actuated cam for biasing a latching tab on said container into latching engagement with said ledge.

17. A secure disposable container assembly according to claim 15 for use in combination with an outer housing wherein:

said top cover has a substantially flat top and said access opening is an elongated horizontally extending slot extending substantially the length of said top cover;

said curved portion of said self dumping closure member extends from said access opening above said top cover for defining a disposable insert mode of said container; and said outer housing has a chamber and an access door for mounting said container in said housing, said housing having a top housing cover with an access slot for alignment with said elongated horizontally extending slot in said top cover of said container, and a curved cowling extending over said access slot and said curved portion of said self-dumping closure member.

18. A secure disposable container assembly according to claim 15 wherein:

in said shipping mode, a shipping carton is disposed in said container, and a banding strap extends around said container and said top cover for holding said top cover in said spaced relation against said carton.

* * * * *